(12) United States Patent
Kuo et al.

(10) Patent No.: US 10,563,040 B2
(45) Date of Patent: Feb. 18, 2020

(54) LOW-TEMPERATURE CURABLE COMPOSITIONS

(71) Applicant: Eastman Chemical Company, Kingsport, TN (US)

(72) Inventors: Thauming Kuo, Kingsport, TN (US); Vasudev R. Bhonde, Johnson City, TN (US); Phillip Bryan Hall, Jonesborough, TN (US)

(73) Assignee: Eastman Chemical Company, Kingsport, TN (US)

( * ) Notice: Subject to any disclaimer, the term of this patent is extended or adjusted under 35 U.S.C. 154(b) by 177 days.

(21) Appl. No.: 15/621,323

(22) Filed: Jun. 13, 2017

(65) Prior Publication Data

US 2018/0355145 A1    Dec. 13, 2018

(51) Int. Cl.
| | |
|---|---|
| C08K 5/07 | (2006.01) |
| C08K 5/053 | (2006.01) |
| C08K 5/092 | (2006.01) |
| C07C 69/38 | (2006.01) |
| C09D 167/02 | (2006.01) |
| C08G 63/91 | (2006.01) |
| C08G 63/16 | (2006.01) |
| C08G 63/20 | (2006.01) |
| C08G 16/04 | (2006.01) |
| C08L 35/02 | (2006.01) |

(52) U.S. Cl.
CPC ............... *C08K 5/07* (2013.01); *C07C 69/38* (2013.01); *C08G 16/04* (2013.01); *C08G 63/16* (2013.01); *C08G 63/20* (2013.01); *C08G 63/914* (2013.01); *C08K 5/053* (2013.01); *C08K 5/092* (2013.01); *C09D 167/02* (2013.01); *C08L 35/02* (2013.01)

(58) Field of Classification Search
CPC .......... C08K 5/07; C08K 5/053; C08K 5/092; C07C 69/38; C08G 16/04; C08G 63/16; C08G 63/20; C08G 63/914; C09D 167/02; C08L 35/02
USPC ...................................................... 525/531
See application file for complete search history.

(56) References Cited

U.S. PATENT DOCUMENTS

| | | | |
|---|---|---|---|
| 4,071,578 A | | 1/1978 | Lasher |
| 4,708,821 A | * | 11/1987 | Shimokawa ............ A61L 9/048 512/12 |
| 6,177,514 B1 | | 1/2001 | Pathak et al. |
| 2002/0040093 A1 | | 4/2002 | Hobel et al. |
| 2005/0081994 A1 | | 4/2005 | Beckley et al. |
| 2007/0048337 A1 | | 3/2007 | Arthur |
| 2008/0135060 A1 | | 6/2008 | Kuo et al. |
| 2013/0233739 A1 | | 9/2013 | Zhao et al. |
| 2016/0115345 A1 | | 4/2016 | Kuo et al. |
| 2016/0137877 A1 | | 5/2016 | Kuo et al. |

FOREIGN PATENT DOCUMENTS

| | | |
|---|---|---|
| DE | 196 20 351 A1 | 11/1997 |
| EP | 0 161 697 A1 | 11/1985 |
| EP | 1 435 383 A1 | 7/2004 |
| JP | S56 5847 A | 1/1981 |
| WO | WO 96/41833 A1 | 12/1996 |

OTHER PUBLICATIONS

Invitation to Pay Additional Fees dated Aug. 23, 2018 received in International Application No. PCT/US2018/036237.
Notification of Transmittal of the International Search Report and the Written Opinion of the International Searching Authority dated Nov. 6, 2018 for International Application No. PCT/US2018/036237.
Notification of Transmittal of the International Search Report and the Written Opinion of the International Searching Authority dated Aug. 24, 2018 for International Application No. PCT/US2018/036244.
Co-pending U.S. Appl. No. 15/621,296, filed Jun. 13, 2017; Kuo et al.
Witzeman et al.; "Comparison of Methods for the Preparation of Acetoacetyiated Coating Resins"; Journal of Coatings Technology; vol. 62; No. 789; pp. 101-112 (1990).
Noomen; "Applications of Michael addition chemistry in coatings technology"; Progress in Organic Coatings; 32; (1997); pp. 137-142.
ASTM D4752-10; Standard Practice for Measuring MEK Resistance of Ethyl Silicate (Inorganic) Zinc-Rich Primers by Solvent Rub, 2016.
Wicks et al.; "Chapter 13—Polyester Resins"; Organic Coatings Science and Technology; 2nd ed.; pp. 246-257; Wiley, New York, 1999.
ASTM D1003; Standard Test Method for Haze and Luminous Transmittance of Transparent Plastics, 2019.
ASTM D2578; Standard Test Method for le ing Tension of Polyethylene and Polypropylene Films, 2019.
ASTM D3236; Standard Test Method for Apparent Viscosity of Hot Melt Adhesives and Coating Materials, 2019.
ASTM D3985; Standard Test Method for Oxygen Gas Transmission Rate Through Plastic Film and Sheeting Using a Coulometric Sensor, 2019.

(Continued)

*Primary Examiner* — David T Karst
(74) *Attorney, Agent, or Firm* — Matthew W. Smith

(57) ABSTRACT

This invention pertains to a curable composition comprising a first component having beta-ketoacetate and/or malonate functionalities and a second component having two or more aldehyde functionalities. The compositions can be cured at room temperature or low temperatures to yield crosslinked networks that are capable of providing desirable properties for coating and adhesive applications. The reactive functionalities of beta-ketoacetate, malonate, and aldehyde can be either on polymers as the main binders or on small molecules as the crosslinkers. The curable compositions desirably are either solventless or organic solvent based.

14 Claims, No Drawings

(56) References Cited

OTHER PUBLICATIONS

ASTM D4366; Standard Test Method for Hardness of Organic Coatings by Pendulum Damping Tests, 2019.
ASTM D5402; Standard Practice for Assessing the Solvent Resistance of Organic Coatings Using Solvent Rubs, 2019.
ASTM D649341; Standard Test Methods for Softening Point of Hydrocarbon Resins and Rosin Based Resins by Automated Ring-and-Ball Apparatus, 2019.
ASTM D7253-16; Standard Test Method for Polyurethane Raw Materials: Determination of Acidity as Acid Number for Polyether Polyols, 2019.
ASTM D974; Standard Test Method for Acid and Base No. By Color-Indicator Titration, 2019.
ASTM E222-17; Standard Test Methods for Hydroxyl Groups Using Acetic Anhydride Acetylation, 2019.
ASTM F1249; Standard Test Method for Water Vapor Transmission Rate Through Plastic Film and Sheeting Using a Modulated Infrared Sensor, 2019.
ASTM F2622; Standard Test Method for Oxygen Gas Transmission Rate Through Plastic Film and Sheeting Using Various Sensors, 2019.
ASTM G155; Standard Practice for Operating Xenon Arc Light Apparatus for Exposure of Non-Metallic Materials, 2019.
Blank et al.; "Delayed (Latent) Catalysis in Coatings;" www.researchgate.net/publication/228420884, 2011.
Office Action dated May 10, 2019 received in co-pending U.S. Appl. No. 15/621,296.

\* cited by examiner

LOW-TEMPERATURE CURABLE COMPOSITIONS

FIELD OF THE INVENTION

This invention pertains to low temperature curing thermoset compositions. More particularly this invention provides polymer compositions having moieties containing activated methylene or methine groups, such as those of beta-ketoacetate and malonate that are curable with compounds having aldehyde functionality at low temperatures to form crosslinked networks. Formulations based on such polymers and aldehyde compounds are especially suitable for low-temperature curing coating and adhesive applications without the use of isocyanates.

BACKGROUND OF THE INVENTION

Thermosetting compositions based on isocyanate crosslinkers are widely used for coating and adhesive applications. Such systems are curable at room temperature or low temperatures (e.g. <80° C.) and are capable of providing the desirable properties for a variety of applications. However, there have been increasing health concerns associated with the production and the use of isocyanate compounds and the formulations based on isocyanates. Thus, there is a need for a crosslinking system that is isocyanate free. Further, it is desirable the system not generate by-products upon crosslinking, which can be detrimental to film formation or other desirable properties. Since the isocyanate crosslinkers are generally used for low-temperature curing, in order to replace them, the new system must be curable at ambient temperatures. This is particularly challenging because organic reactions generally require the use of heat to overcome the energy that is needed for the reactions to occur. This invention provides a novel crosslinking system that is isocyanate free, curable at low temperatures, has no VOC's or low VOC's (volatile organic compounds), and is suitable for applications in coatings, such as automotive, industrial maintenance, and furniture, and in adhesives such as laminating adhesive. The low-temperature curable composition is especially suitable for field-applied industrial maintenance coatings, automotive refinish coatings, and marine craft gelcoats.

SUMMARY OF THE INVENTION

In one embodiment, the invention provides a curable composition comprising: (I) a first component having two or more functional groups selected from the group consisting of β-ketoacetate and malonate functional groups; (II) a second component having two or more aldehyde functional groups; and (III) a basic catalyst.

In another embodiment, the invention provides a curable composition comprising:
I. a polyester comprising the residues of:
  a. a hydroxyl component comprising:
    i. a diol in an amount ranging from 70 to 100 mole %, based on the total moles of (i) and (ii); and
    ii. a polyol in an amount ranging from 0 to 30 mole %, based on the total moles of (i) and (ii); and
  b. malonic acid, its ester, or a combination thereof; and
  c. optionally a carboxyl component, other than malonic acid or its ester, comprising a polycarboxylic acid compound, a derivative of polycarboxylic acid compound, or a combination thereof;

II. an aldehyde component selected from the group consisting of 1,3-cyclohexanedicarboxaldehyde (1,3-CHDAL), 1,4-cyclohexanedicarboxaldehyde (1,4-CHDAL), mixtures of 1,3- and 1,4-CHDAL, 2,6-norbornanedicarboxaldehyde, 2,5-norbornanedicarboxaldehyde, cyclododecane-1,4,8-tricarbaldehyde, 3,(4-formylcyclohexyl)propanal, and their isomers; and
III. a basic catalyst which is one or more selected from the group consisting of 1,8-diazabicyclo-[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), 1,1,3,3-tetramethylguanidine (TMG), 1,4-diazabicyclo[2.2.2]octane (DABCO), triethylamine, N,N-dimethylethanolamine, ammonium hydroxide, triphenyl phosphine, and tributyl phosphine.

In another embodiment the invention provides a curable composition comprising:
I. an acetoacetate functional polyester comprising the residues of:
  a. a hydroxyl component comprising:
    i. a diol in an amount ranging from 70 to 100 mole %, based on the total moles of (i) and (ii); and
    ii. a polyol in an amount ranging from 0 to 30 mole %, based on the total moles of (i) and (ii);
  b. a carboxyl component comprising a polycarboxylic acid compound, a derivative of polycarboxylic acid compound, or a combination thereof; and
  c. an alkyl acetoacetate, a diketene, or a combination thereof in an amount ranging from about 5 to about 50 weight %, based on the total weight of (a), (b), and (c);
II. an aldehyde component selected from the group consisting of 1,3-cyclohexanedicarboxaldehyde (1,3-CHDAL), 1,4-cyclohexanedicarboxaldehyde (1,4-CHDAL), mixtures of 1,3- and 1,4-CHDAL, 2,6-norbornanedicarboxaldehyde, 2,5-norbornanedicarboxaldehyde, cyclododecane-1,4,8-tricarbaldehyde, 3,(4-formylcyclohexyl)propanal, and their isomers; and
III. a basic catalyst is one or more selected from the group consisting of 1,8-diazabicyclo-[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), 1,1,3,3-tetramethylguanidine (TMG), 1,4-diazabicyclo[2.2.2]octane (DABCO), triethylamine, N,N-dimethylethanolamine, ammonium hydroxide, triphenyl phosphine, and tributyl phosphine.

DETAILED DESCRIPTION

Unless otherwise indicated, all numbers expressing quantities of ingredients, properties such as molecular weight, reaction conditions, and so forth used in the specification and claims are to be understood as being modified in all instances by the term "about." Unless indicated to the contrary, the numerical parameters set forth in the following specification and attached claims are approximations that may vary depending upon the desired properties sought to be obtained by the present invention. At the very least, each numerical parameter should be construed in light of the number of reported significant digits and by applying ordinary rounding techniques. Further, the ranges stated in this disclosure and the claims are intended to include the entire range specifications and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in its respective testing measurements.

As used in the specification and the appended claims, the singular forms "a," "an" and "the" include their plural referents unless the context clearly dictates otherwise. For example, a reference to a "polyester," a "dicarboxylic acid", a "residue" is synonymous with "at least one" or "one or more" polyesters, dicarboxylic acids, or residues and is thus intended to refer to both a single or plurality of polyesters, dicarboxylic acids, or residues. In addition, references to a composition containing or including "an" ingredient or "a" polyester is intended to include other ingredients or other polyesters, respectively, in addition to the one named. The terms "containing" or "including" are intended to be synonymous with the term "comprising", meaning that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims.

Also, it is to be understood that the mention of one or more process steps does not preclude the presence of additional process steps before or after the combined recited steps or intervening process steps between those steps expressly identified.

The present inventors have discovered that polyesters having moieties containing activated methylene or methine groups, such as those of beta-ketoacetate and malonate, are curable with compounds having aldehyde functionality at low temperatures to form crosslinked networks. Formulations based on such polyesters and aldehyde compounds are especially suitable for low-temperature curing coating and adhesive applications without the use of isocyanates.

Thus, in one embodiment, this invention provides a curable composition comprising:
I) a first component having two or more functional groups selected from beta-ketoacetate and malonate,
II) a second component having two or more aldehyde functional groups, and
III) a basic catalyst.

The first component may be either a polymer or a compound having two or more functional groups selected from beta-ketoacetate (1) and malonate (2) with the formulae below, wherein R is a branched or straight chain, saturated or unsaturated alkyl, alicyclic, or aromatic group; R' is a hydrogen or a branched or straight chain, saturated or unsaturated alkyl, alicyclic, or aromatic group.

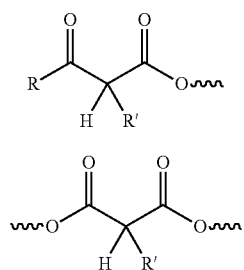

In one aspect, the equivalent ratio of the ketoacetate and/or malonate functionalities in the first component and the aldehyde functionality in the second component (i.e. eq. of ketoacetate and/or malonate/eq. of aldehyde) is from about 1.2 to about 0.9, or from about 1.1 to about 0.95, or from about 1.05 to about 1.0.

In another embodiment, the first component is a polyester having two or more beta-ketoacetate groups, represented by Formula 3, wherein Z is a polyester residue, n represents the average number of beta-ketoacetate groups per polymer chain and is an average of at least 2. In one aspect, the beta-ketoacetate group is acetoacetate (AcAc), and the polyester is an acetoacetate-functional polyester.

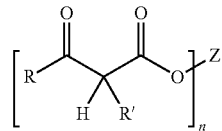

The acetoacetate-functional polyester may be prepared by reacting a polyester resin containing hydroxyl groups, for example, a polyester having a hydroxyl number of at least 5, desirably about 30 to 200, with diketene or a compound having the beta-ketoacetate moiety such as t-butylacetoacetate (tBAA). Various methods for the preparation of acetoacetylated polyester coating resins have been described by Witzeman et al. in the Journal of Coatings Technology, Vol. 62, No. 789, pp. 101-112 (1990). Suitable amounts of each in a reaction mixture include from about 50 to about 95, 60 to 90, 65 to 85, or 70 to 80 wt. % of the polyester resin and from about 5 to about 50, 10 to 40, 15 to 35, or 20 to 30 wt. % of the compound having a beta-ketoacetate moiety or a diketene can be reacted together, wherein the weight percents are based on the total weight of the polyester resin and the compound having the beta-ketoacetate moiety.

In another embodiment, the first component is a polyester having two or more malonate groups (Formula 2). Such malonate-functional polyesters may be prepared by using malonic acid or its ester, such as dimethyl malonate or diethyl malonate, as one of the diacids in a polyester synthesis.

In still another embodiment, the first component is a vinyl polymer having two or more beta-ketoacetate functional groups. Such a vinyl polymer may be prepared by using an acrylate monomer having beta-ketoacetate functionality, such as acetoacetyl ethyl methacrylate (AAEM) or acetoacetyl ethyl acrylate, as one of the ethylenically unsaturated monomers for vinyl polymer synthesis.

Said ethylenically unsaturated monomers suitable for copolymerization with acetoacetyl ethyl methacrylate (AAEM) or acetoacetyl ethyl acrylate include styrene, methyl acrylate, methyl methacrylate, ethyl acrylate, ethyl methacrylate, n-butyl acrylate, n-butyl methacrylate, isobutyl acrylate, isobutyl methacrylate, t-butyl acrylate, t-butyl methacrylate, 2-ethylhexyl acrylate, 2-ethylhexyl methacrylate, acrylic acid, methacrylic acid, itaconic acid, crotonic acid, maleic anhydride, allyl methacrylate, isobornyl methacrylate, methacrylamide, acrylamide, butyl acrylamide, ethyl acrylamide, N,N-dimethylaminoethyl acrylate, isoprene, octyl acrylate, octyl methacrylate, iso-octyl acrylate, and iso-octyl methacrylate.

Said vinyl polymer may be prepared by bulk or solution polymerization in an organic solvent by a method known in the art, such as free radical polymerization, anionic, or cationic polymerization using various initiators.

In a further embodiment, the second component is a small molecule or an adduct having two or more aldehyde functional groups. Examples of such aldehydes include 1,3-cyclohexanedicarboxaldehyde (1,3-CHDAL), 1,4-cyclohexanedicarboxaldehyde (1,4-CHDAL), mixtures of 1,3- and 1,4-CHDAL (Formula 4) such as Paraloid Edge XL-195 available from Dow, 2,6-norbornanedicarboxaldehyde, 2,5-norbornanedicarboxaldehyde, cyclododecane-1,4,8-tricarbaldehyde, 3,(4-formylcyclohexyl)propanal, and their isomers.

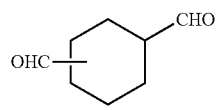

4

Said multi-functional aldehyde compounds may be blocked to improve storage stability and/or extend the open time for application of the curable composition of the invention. The aldehyde may be reacted with a diol such as ethylene glycol to form a dioxolane, with an amine to form an imine, with hydroxylamine to form an oxime, or with sodium bisulfite to form a sulfonate salt. The resulting blocked aldehydes may be de-blocked by changing the pH or heating. The techniques for blocking and de-blocking of a polyaldehyde have been disclosed in U.S. Pat. No. 6,177,514.

In yet another embodiment, the first component of the curable composition of the present invention is an adduct having two or more β-ketoacetate functional groups such as, for example, 2,2,4,4-tetramethylcyclobutane-1,3-diol diacetoacetate, glycerol triacetoacetate, trimethylpropane triacetoacetate, pentaerythritol tetraacetoacetate. In still another embodiment, the second component is a vinyl polymer having two or more aldehyde functional groups. Such vinyl polymers having two or more aldehyde functional groups can be prepared by using acrolein or methacrolein as one of the ethylenically unsaturated monomers for vinyl polymer synthesis. Said ethylenically unsaturated monomers suitable for copolymerization with acrolein or methacrolein include styrene, methyl acrylate, methyl methacrylate, ethyl acrylate, ethyl methacrylate, n-butyl acrylate, n-butyl methacrylate, isobutyl acrylate, isobutyl methacrylate, t-butyl acrylate, t-butyl methacrylate, 2-ethylhexyl acrylate, 2-ethylhexyl methacrylate, acrylic acid, methacrylic acid, itaconic acid, crotonic acid, maleic anhydride, allyl methacrylate, isobornyl methacrylate, methacrylamide, acrylamide, butyl acrylamide, ethyl acrylamide, N,N-dimethylaminoethyl acrylate, isoprene, octyl acrylate, octyl methacrylate, iso-octyl acrylate, and iso-octyl methacrylate.

Said vinyl polymer may be prepared by bulk or solution polymerization in an organic solvent by a method known in the art, such as free radical polymerization, anionic, or cationic polymerization using various initiators. The vinyl polymer may also be prepared by emulsion polymerization in water.

In a further embodiment, the first component of the curable composition of the present invention is an adduct having two or more β-ketoacetate functional groups, and the second component is a vinyl polymer having two or more aldehyde functional groups.

In another embodiment, the acetoacetate functional polyester comprises the reaction product (or residues) of (a) from about 50 to about 95 weight percent of a hydroxyl functional polyester and (b) from about 5 to about 50 weight percent of an alkyl acetoacetate or diketene, wherein the weight percents are based on the total weight of (a) and (b).

The hydroxyl functional polyester of component (a) has a hydroxyl number of at least 5 mgKOH/g; the preferred hydroxyl number is 30 to 200 and the most preferred being 50 to 150. The weight % of (a) may be 50 to about 95, 60 to 90, 65 to 85, or 70 to 80 and (b) may be 5 to about 50, 10 to 40, 15 to 35, or 20 to 30. Desirably, the acid number of the hydroxyl functional polyester is from 0 to about 15, from 0 to about 10, or from 0 to 5 mg KOH/g. Low acid numbers are desirable since the curable composition of the invention requires the use of a base catalyst. Higher acid numbers can deactivate the base catalyst.

The glass transition temperature (Tg) of the acetoacetate-functional polyester of the present invention may be from −40° C. to 120° C., from −10° C. to 100° C., from 20° C. to 80° C., or from 30° C. to 70° C. Depending on the applications, the polyesters can preferably have low Tg's or high Tg's. For example, low Tg polyesters are more desirable for adhesive applications, while high Tg polyesters are more desirable for coating applications.

The weight average molecular weight (Mw) of the acetoacetate functional polyester of the present invention may be from 1,000 to 100,000; from 1,500 to 50,000; from 2,000 to 10,000; or from 2,500 to 5,000 g/mole. The polyester may be linear or branched. The Mw is measured by gel permeation chromatography (GPC) using polystyrene equivalent molecular weight.

The hydroxyl functional polyester that is used to prepare acetoacetate polyester is typically synthesized by reacting a hydroxyl compound, for example, a diol or triol, with a carboxyl compound, for example, a dicarboxylic acid. Examples of hydroxyl compounds include diols such as 2,2,4,4-tetraalkylcyclobutane-1,3-diol (TACD), 2,2-dimethyl-1,3-propanediol (neopentyl glycol), 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 2-ethyl-2-isobutyl-1,3-propanediol, 1,3-butanediol, 1,4-butanediol, 1,5-pentanediol, 1,6-hexanediol, 2,2,4,4-tetramethyl-1,6-hexanediol, 1,10-decanediol, 1,4-benzenedimethanol, hydrogenated bisphenol A, ethylene glycol, propylene glycol, diethylene glycol, dipropylene glycol, triethylene glycol, tetraethylene glycol, and polyethylene glycol, and polyols such as 1,1,1-trimethylol propane, 1,1,1-trimethylolethane, glycerin, pentaerythritol, erythritol, threitol, dipentaerythritol, sorbitol, and the like.

Examples of said 2,2,4,4-tetraalkylcyclobutane-1,3-diols (TACD) include 2,2,4,4-tetramethylcyclobutane-1,3-diol (TMCD), 2,2,4,4-tetraethylcyclobutane-1,3-diol, 2,2,4,4-tetra-n-propylcyclobutane-1,3-diol, and 2,2,4,4-tetra-n-butylcyclobutane-1,3-diol.

The carboxyl compound may be a polycarboxylic acid compound, a derivative of polycarboxylic acid compound, or a combination thereof. Suitable polycarboxylic acid compounds include compounds having at least two carboxylic acid groups. In one aspect, the polycarboxylic acid compound comprises a dicaraboxylic acid compound having two carboxylic acid groups, derivatives thereof, or combinations thereof, capable of forming an ester linkage with a polyhydroxyl component. For example, a polyester can be synthesized by using a polyhydroxyl compound and a derivative of a dicarboxylic acid such as, for example, dimethyl ester or other dialkyl esters of the diacid, or diacid chloride or other diacid halides, or acid anhydride. In another aspect, the polycarboxylic acid compound comprises a tricarboxylic acid or anhydride, for example, trimellitic acid or trimellitic anhydride.

Examples of dicarboxylic acids that may be used include aliphatic dicarboxylic acids, alicyclic dicarboxylic acids, aromatic dicarboxylic acids, derivatives of each, or mixtures of two or more of these acids. Thus, suitable dicarboxylic acids include, but are not limited to, isophthalic acid (or dimethyl isophthalate), terephthalic acid (or dimethyl terephthalate), phthalic acid, phthalic anhydride, 1,4-cyclohexane-dicarboxylic acid, 1,3-cyclohexanedicarboxylic acid, hexahydrophthalic anhydride, tetrahydrophthalic anhydride, tetrachlorophthalic anhydride, dodecanedioic acid, sebacic acid, azelaic acid, maleic acid or anhydride, fumaric acid, succinic anhydride, succinic acid, adipic acid, 2,6-naphthalenedicarboxylic acid, glutaric acid, itaconic acid, and their derivatives, diglycolic acid; 2,5-norbornanedicarboxylic acid; 1,4-naphthalenedicarboxylic acid; 2,5-naphthalenedicarboxylic acid; diphenic acid; 4,4'-oxydibenzoic acid; 4,4'-sulfonyidibenzoic acid, and mixtures thereof.

In one embodiment, the acetoacetate functional polyester comprises the residues of:
a. a hydroxyl component comprising
   i. a diol in an amount ranging from 70 to 100 mole %, based on the total moles of (i) and (ii), and
   ii. a polyol in an amount ranging from 0 to 30 mole %, based on the total moles of (i) and (ii),
b. a carboxyl component comprising a polycarboxylic acid compound, a derivative of polycarboxylic acid compound, or a combination thereof, and
c. an alkyl acetoacetate and/or diketene in an amount ranging from about 5 to about 50 weight %, based on the total weight of (a), (b), and (c).

The mole % of the diol component of (a)(i) can be 70 to 100, 80 to 97, or 85 to 95, and the polyol of (a)(ii) can be 0 to 30, 3 to 20, or 5 to 15.

Preferably, the diol (a)(i) comprises one or more selected from the group consisting of 2,2,4,4-tetramethylcyclobutane-1,3-diol, 2,2-dimethyl-1,3-propanediol (neopentyl glycol), 1,2-cyclohexanedimethanol, 1,3-cyclohexanedimethanol, 1,4-cyclohexanedimethanol, 2,2,4-trimethyl-1,3-pentanediol, hydroxypivalyl hydroxypivalate, 2-methyl-1,3-propanediol, 2-butyl-2-ethyl-1,3-propanediol, 1,4-butanediol, and 1,6-hexanediol. Preferably, the polyol (a)(ii) is selected from 1,1,1-trimethylol propane, 1,1,1-trimethylolethane, glycerin, and pentaerythritol.

Preferably, the carboxyl component (b) comprises one or more selected from the group consisting of isophthalic acid (or dimethyl isophthalate), terephthalic acid (or dimethyl terephthalate), phthalic acid, phthalic anhydride, 1,4-cyclohexane-dicarboxylic acid, 1,3-cyclohexanedicarboxylic acid, adipic acid, 2,6-naphthalenedicarboxylic acid, 1,4-naphthalenedicarboxylic acid; 2,5-naphthalenedicarboxylic acid; hexahydrophthalic anhydride, tetrahydrophthalic anhydride, trimellitic anhydride, maleic acid or anhydride, fumaric acid, succinic anhydride, and succinic acid. Most preferably, the carboxyl compound (b) is selected from the group consisting of isophthalic acid (or dimethyl isophthalate), terephthalic acid (or dimethyl terephthalate), phthalic acid, phthalic anhydride, 1,4-cyclohexanedicarboxylic acid, 1,3-cyclohexanedicarboxylic acid, adipic acid, hexahydrophthalic anhydride, maleic anhydride, and succinic anhydride.

Examples of said alkyl acetoacetate (c) include t-butyl acetoacetate, methyl acetoacetate, ethyl acetoacetate, n-propyl acetoacetate, isopropyl acetoacetate, n-butyl acetoacetate, and the like.

The malonate-functional polyester is a polyester having malonic acid or its ester, such as dimethyl malonate or diethyl malonate, as one of the diacid components. Desirably, the malonate-functional polyester is a hydroxyl functional polyester as described previously.

Thus, in one embodiment, the malonate-functional polyester comprises the residues of
a. a hydroxyl component comprising
   i. a diol in an amount ranging from 70 to 100 mole %, based on the total moles of (i) and (ii), and
   ii. a polyol in an amount ranging from 0 to 30 mole %, based on the total moles of (i) and (ii), and
b. malonic acid, its ester, or a combination thereof, and
c. optionally a carboxyl component, other than malonic acid or its ester, comprising a polycarboxylic acid compound, a derivative of polycarboxylic acid compound, or a combination thereof.

The hydroxyl component (a) and the carboxyl component (c) are the same as defined in the description of the hydroxyl functional polyester. In one embodiment, malonic acid (b) is in an amount of about 5 to 80 mole % based on the total carboxyl components, (b) and (c), or 10 to 70, or 15 to 60, or 20 to 50, or 25 to 45, or 30 to 40 mole %.

In another embodiment, the malonate-functional polyester is further reacted with a β-ketoacetate compound or diketene to yield a polyester having both malonate and β-ketoacetate functional groups.

The curable composition of the present invention further comprises a base catalyst (III) in an amount ranging from 0.1 to 10, 0.2 to 7, 0.3 to 6, or 0.5 to 5 weight %, based on the total weight of the first component (I) and the second component (II).

Examples of the base catalyst include amidine type, such as 1,8-diazabicyclo-[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), and 1,1,3,3-tetramethylguanidine (TMG), bicyclic unhindered tertiary amine type such as 1,4-diazabicyclo[2.2.2]octane (DABCO), tertiary amine type such as triethylamine and N,N-dimethylethanolamine, quaternary ammonium compounds such as ammonium hydroxide and tetrabutyl ammonium hydroxide, phosphine type such as triphenyl phosphine and tributyl phosphine, and inorganic bases such as sodium hydroxide and potassium hydroxide, and mixtures thereof. The amidine type, the bicyclic unhindered tertiary amine type, and the tertiary amine type are more desirable. The most desirable catalyst is the amidine type, such as 1,8-diazabicyclo-[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), and 1,1,3,3-tetramethylguanidine (TMG).

In order to extend the pot life of the curable composition of the invention, the base catalyst (III) may be temporarily blocked. For example, an alcohol such as methanol, ethanol, n-propanol, isopropanol may be added to the composition on storage to block the catalyst. When the composition is applied, the alcohol will evaporate and the catalyst de-blocked. A carboxylic acid, such as benzoic acid, acetic acid, formic acid, or cyanoacetic acid, can also be added to the composition to block the catalyst and subsequently deblock by heating. Such techniques for blocking and deblocking the amidine catalysts have been disclosed in Progress in Organic Coatings, 32 (1997), 137-142 by Arie Noomen.

Thus, in a further embodiment, the curable composition of the present invention further comprises a catalyst-blocking agent. Examples of such blocking agents include alcohols, such as methanol, ethanol, isopropanol, n-propanol, and the like, and carboxylic acids such as benzoic acid, formic acid, acetic acid, and cyanoacetic acid.

In still another embodiment, this invention provides a curable composition comprising an acetoacetate- and/or malonate-functional polyester and one or more dialdehydes selected from 1,3-cyclohexanedicarboxaldehyde (1,3-CH-DAL), 1,4-cyclohexanedicarboxaldehyde (1,4-CHDAL), and mixtures of 1,3- and 1,4-CHDAL. In one aspect, the equivalent ratio of the acetoacetate and/or malonate functionalities and the aldehyde (CHO) functionality (i.e. eq. ratio of AcAc/CHO) is from about 1.05 to about 1.0.

The curable composition of the invention is capable of reacting at an ambient temperature in the presence of a base catalyst. In a so-called 2K system, it is required to mix the two components shortly before use to prevent the composition from premature crosslinking and becoming useless. In the present invention, the mixing of the two components does not result in significant reactions in the absence of a catalyst. Thus, the first component and the second component may be mixed and stored until the mixture is ready to be used. The base catalyst can then be added shortly before use.

The curable composition of the invention may be solventless or solvent-based. The solvent-based composition further comprises an organic solvent. Suitable organic solvents include xylene, ketones (for example, methyl amyl ketone and methyl ethyl ketone), 2-butoxyethanol, ethyl-3-ethoxypropionate, toluene, butanol, cyclopentanone, cyclohexanone, ethyl acetate, butyl acetate, and other volatile inert solvents typically used in industrial coatings.

The amount of solvents can range from 0% to 70%, 5% to 50%, or 10% to 30% based on the total weight of the curable composition.

In one embodiment, the curable composition of the present invention is a coating composition suitable for applications in coatings such as automotive, industrial maintenance, metal can, architecture, and furniture. The curing temperature for such coating applications can range from room temperature to about 230° C. The low-temperature curable composition is especially suitable for field-applied industrial maintenance coatings, automotive refinish coatings, and marine craft gelcoats.

In another embodiment, the curable composition of the present invention is an adhesive composition for applications in adhesives such as laminating adhesive for flexible packaging. The curing temperature for such an adhesive is desirably a low temperature ranging from room temperature to about 80° C.

The curable composition of this invention may further comprise an amino crosslinker and/or phenolic resin. Suitable amino crosslinkers include hexamethoxymethylmelamine, tetramethoxymethylbenzoguanamine, tetramethoxymethylurea, mixed butoxy/methoxy substituted methyl melamines, and the like. Suitable phenolic resins include Phenodur PR371/70B, PHENODUR® PR 516/60B, PHENODUR® PR 612/80B available from Allnex.

In addition to coating and adhesive applications, the curable composition of this invention can also be used for other applications, such as plastic molding and rubber compounding, where forming polymeric network is desirable.

After formulation, the curable composition can be applied to a substrate or article. Thus, a further aspect of the present invention is a shaped or formed article that has been coated with the curable compositions of the present invention. The substrate can be any common substrate such as paper; polymer films such as polyethylene or polypropylene; wood; metals such as aluminum, steel or galvanized sheeting; glass; urethane elastomers; primed (painted) substrates; and the like. The curable composition can be coated onto a substrate using techniques known in the art, for example, by spraying, draw-down, roll-coating, etc., to form a dried coating having a thickness of about 0.1 to about 4 mils (1 mil=25 µm), or 0.5 to 3, or 0.5 to 2, or 0.5 to 1 mils on the substrate. The coating can be cured at ambient temperatures such as room temperature or by heating to a temperature of about 50° C. to about 200° C. for a time period that typically ranges from about a few seconds to about 60 minutes and allowed to cool. When used as an adhesive, the curable composition can be applied to bond the objects by a method known in the art such as brushing, spraying, nozzle dispensing, roll coating, printing, and curtain coating.

EXAMPLES

Example 1. Synthesis of Acetoacetate Functional Polyester 1 (AcAc Polyester 1)

Hydroxyl Functional Polyester 1:

A 2-L kettle with a four-neck lid was equipped with a mechanical stirrer, a thermocouple, a heated partial condenser (115° C.), a Dean-Stark trap, and a chilled condenser (15° C.). To the flask were charged 1,6-hexanediol (290.4 g), 2-methyl-1,3-propanediol (221.4 g), trimethylolpropane (48.84 g), adipic acid (613.8 g), and the acid catalyst, Fascat-4100 (Arkema Inc.) (0.84 g). The reaction was allowed to react under nitrogen at 170° C. for 2 hours and at 220° C. for about 3 hours to yield a clear, viscous mixture. A total of 144 g of the distillate was collected in the Dean-Stark trap. The resulting mixture was allowed to cool to room temperature and subsequently collected (1003 g). Acid number: <1.0 mgKOH/g; hydroxyl number: 128.5 mgKOH/g; glass transition temperature (Tg): −66.6° C.; number average molecular weight (Mn): 1865 g/mole; weight average molecular weight (Mw): 4047 g/mole.

Acetoacetate Functional Polyester 1:

The next synthesis was aimed to convert hydroxyl number of 50 mgKOH/g of the above hydroxyl functional polyester (1) to acetoacetate number of 50 mgKOH/g. To a 500 mL, three-neck, round-bottom flask equipped with a mechanical stirrer, a heated partial condenser, a Dean-Stark trap, and a water condenser were added the above hydroxyl-functional polyester 1 (100.0 g) and t-butyl acetoacetate (14.08 g). The mixture was gradually heated and allowed to react at 120° C. for 20 minutes and at 140'C for two hours. A total of 6.5 ml of the condensate (t-butanol) was collected in the Dean-Stark adapter. The resulting viscous resin was allowed to cool and subsequently collected. Glass transition temperature (Tg): −65.4° C.; number average molecular weight (Mn): 1724 g/mole; weight average molecular weight (Mw): 3976 g/mole.

Example 2. Synthesis of Acetoacetate Functional Polyester 2 (AcAc Polyester 2)

The next synthesis was aimed to convert hydroxyl number of 100 mgKOH/g of the above hydroxyl functional polyester (1) to acetoacetate number of 100 mgKOH/g. To a 500 mL, three-neck, round-bottom flask equipped with a mechanical stirrer, a heated partial condenser, a Dean-Stark trap, and a water condenser were added the above hydroxyl-functional polyester 1 (100.0 g) and t-butyl acetoacetate (28.16 g). The mixture was gradually heated and allowed to react at 120° C. for 20 minutes and at 140° C. for two hours. A total of 15 ml of the condensate (t-butanol) was collected in the Dean-Stark adapter. The resulting viscous resin was allowed to cool and subsequently collected. Glass transition temperature (Tg): −64.7° C.; number average molecular weight (Mn): 1667 g/mole; weight average molecular weight (Mw): 3933 g/mole.

Example 3. Synthesis of Acetoacetate Functional Polyester 3 (AcAc Polyester 3)

A hydroxyl functional polyester (2) with the composition of 2,2,4,4-tetramethyl-13-cyclobutanediol, neopentyl glycol, trimethylolpropane, hexahydrophthalic anhydride and adipic acid was prepared similarly as described in Example 1. The polyester had the properties of: acid number 10 mgKOH/g, hydroxyl number 130 mgKOH/g, and Tg 2° C. The next synthesis was aimed to convert hydroxyl number of 100 mgKOH/g of the above hydroxyl functional polyester (2) to acetoacetate number of 100 mgKOH/g. To a 500 mL, three-neck, round-bottom flask equipped with a mechanical stirrer, a heated partial condenser, a Dean-Stark trap, and a water condenser were added the above hydroxyl-functional polyester 2 (100.0 g) and t-butyl acetoacetate (28.16 g). The mixture was gradually heated and allowed to react at 120° C. for 20 minutes and at 140° C. for two hours. A total of 15 ml of the condensate (t-butanol) was collected in the Dean-Stark adapter. The resulting viscous resin was allowed to cool and subsequently collected. Glass transition temperature (Tg): −7.5° C.; number average molecular weight (Mn): 2323 g/mole; weight average molecular weight (Mw): 9169 g/mole.

Example 4. Formulation and Evaluation of Curable Compositions

Formulations 1-8 were prepared by using liquid like AcAc polyesters 1 and 2 without solvents and AcAc polyester 3 in xylene (50%) and the crosslinker, a mixture of 1,3- and 1,4-cyclohexanedicarboxaldehyde (CHDAL). Three base catalysts were used respectively for evaluating their effects on curing; they were 1,8-diazabicyclo-[5.4.0]undec-7-ene (DBU) (neat), DBU in n-PrOH (25 weight %), and triethylamine (neat). As listed in Table 1, various levels of the catalysts were used, for example, 0.6% and 2% by weight, based on the total weight of polyester and CHDAL.

Each polyester was first mixed with CHDAL at 1:1 equivalent ratio of AcAc/CHO functionalities; a catalyst was added and mixed well just before the coating preparation. The coatings were prepared by applying each formulation to cold-rolled stainless steel panels with a drawdown bar. The coated panels were then allowed to dry at room temperature; the dried coatings had the thickness of about 50 μm for those without solvents and about 25 μm for those with 50% xylene. It was observed that the formulations in the vials could become very viscous, gel-like, and rubbery over several hours, depending on the crosslinking efficiency of the formulations. As indicated in Table 2, AcAc polyesters 2 and 3 having acetoacetate number 100 were more reactive than AcAc polyester 1 with acetoacetate number 50. It should be noted that more base catalysts were used for AcAc polyester 3 since it had a higher acid number (10 vs. <1) and thus needs to be compensated. DBU clearly was a more effective base catalyst than triethylamine, while DBU in n-PrOH slightly slowed down the curing as opposed to DBU without an alcohol solvent. It was also observed that the coating based on AcAc polyester 3 was the only one dried enough for testing pendulum hardness and MEK double rubs, presumably because AcAc polyester 3 had a much higher Tg (−7.5° C. vs. −65° C.). Although the hardness of the dried coating was low after one week, results from the MEK double rubs showed the dried films had a moderate solvent resistance, indicating the occurrence of crosslinking. Tables 3 and 4 show the crosslinking efficiency was increased when the catalyst level was increased from 0.6% to 1% and then to 2%.

TABLE 1

Formulations Based on Various AcAc Polyesters

| Formulation | Polyester | Targeted AcAc Number | Polyester Solution | Polyester solution wt. grams | CHDAL, grams | AcAc/ CHO eq. ratio | Catalyst, DBU, grams | Catalyst, 25% DBU in n-PrOH, grams | Catalyst, Triethylamine, grams |
|---|---|---|---|---|---|---|---|---|---|
| 1 | AcAc Polyester 2 | 100 | 100% | 5.00 | 0.62 | 1/1 | 0.034 (0.6%) | | |
| 2 | AcAc Polyester 1 | 50 | 100% | 5.00 | 0.31 | 1/1 | 0.034 (0.6%) | | |
| 3 | AcAc Polyester 3 | 100 | 50% in xylene | 10.00 | 0.62 | 1/1 | 0.27 (Excess due to high AN) | | |
| 4 | AcAc Polyester 2 | 100 | 100% | 5.00 | 0.62 | 1/1 | | 0.136 (0.6%) | |
| 5 | AcAc Polyester 1 | 50 | 100% | 5.00 | 0.31 | 1/1 | | 0.136 (0.64%) | |
| 6 | AcAc Polyester 3 | 100 | 50% in xylene | 10.00 | 0.62 | 1/1 | | 1.08 (4.8%, excess) | |
| 7 | AcAc Polyester 2 | 100 | 100% | 5.00 | 0.62 | 1/1 | | | 0.11 (2%) |
| 8 | AcAc Polyester 3 | 100 | 50% in xylene | 10.00 | 0.62 | 1/1 | | | 0.27 (4.8%) |

TABLE 2

Drying Characteristics of Various Curable Compositions over Time at Room Temperature

| Formulation | Formulation Observation | | Coating Observation | | | | | Coating Properties | |
|---|---|---|---|---|---|---|---|---|---|
| | Right after mixing with the base catalyst | After one hour | After 3-4 hours | Overnight, (after about 20 hours) | After 2 days | After 3-4 hours | Overnight, (after about 20 hours) | Pendulum hardness after one week | MEK double rubs after one week |
| 1 | clear, viscous; slightly yellow | set up | Clear, set up | Clear, set up | hazy gel-rubbery soft | wet | wet | N/A | N/A |
| 2 | clear, viscous; slightly yellow | very viscous | clear, flow slowly | clear, hardly flow | clear, hardly flow | wet | wet | N/A | N/A |
| 3 | clear, thin; slightly yellow | set up | hazy, slightly yellow, set up | hazy, slightly yellow, set up | hazy, rubbery | non-tacky | glossy, some streaks | 28 | 35 |
| 4 | clear, viscous | flow very slowly | clear, flow very slowly | clear, hardly flow | clear, sticky gel | wet | wet | N/A | N/A |
| 5 | clear, viscous | very viscous | clear, flow slowly | clear, flow very slowly | clear, flow very slowly | wet | wet | N/A | N/A |
| 6 | clear, thin | pourable | clear, slightly yellow, set up | clear, slightly yellow, set up | clear, rubbery, soft | non-tacky | glossy, smooth | 28 | 40 |
| 7 | clear, viscous | very viscous | clear, flow slowly | clear, flow very slowly | clear, sticky gel | wet | wet | N/A | N/A |
| 8 | clear, thin | pourable | clear, thin | clear, flow freely | hazy, soft gel | tacky | tacky | N/A | N/A |

TABLE 3

Formulations with Variation in Catalyst Level

| Formulation | Polyester | Targeted AcAc Number | Polyester Solution | Polyester solution wt. grams | CHDAL, grams | AcAc/ CHO eq. ratio | Catalyst, 25% DBU in n-PrOH, grams |
|---|---|---|---|---|---|---|---|
| 9 | AcAc Polyester 2 | 100 | 100% | 5.00 | 0.62 | 1/1 | 0.22 (1%) |
| 10 | AcAc Polyester 1 | 50 | 100% | 5.00 | 0.31 | 1/1 | 0.21 (1%) |
| 11 | AcAc Polyester 2 | 100 | 100% | 5.00 | 0.62 | 1/1 | 0.44 (2%) |
| 12 | AcAc Polyester 1 | 50 | 100% | 5.00 | 0.31 | 1/1 | 0.42 (2%) |

TABLE 4

Drying Characteristics of Formulations with Various Catalyst Levels

| Formulation | Formulation Observation | | | Coating Observation | | |
|---|---|---|---|---|---|---|
| | Right after mixing with the base catalyst | After one hour | After 3-4 hours | Overnight, (after about 20 hours) | After 3-4 hours | Overnight, (after about 20 hours) |
| 9 | clear, yellow; viscous | extremely viscous | set up | hazy, rubbery, soft | wet | wet |
| 10 | clear; viscous | extremely viscous | extremely viscous | clear, flow very slowly | wet | wet |
| 11 | clear, yellow; viscous | extremely viscous | set up | clear, rubbery | wet | tacky |
| 12 | clear; viscous | extremely viscous | extremely viscous | clear, flow slowly | wet | wet |

Example 5. Synthesis of Malonate Functional Polyester (Malonate Polyester)

A 2-L kettle with a four-neck lid was equipped with a mechanical stirrer, a thermocouple, a heated partial condenser (115° C.), a Dean-Stark trap, and a chilled condenser (15° C.). To the flask were charged 1,6-hexanediol (268 g), 2-methyl-1,3-propanediol (204.4 g), trimethylolpropane (45.08 g), adipic acid (306.9 g), dimethyl malonate (277.4 g), and the acid catalyst, Fascat-4100 (Arkema Inc.) (0.78 g). The reaction was allowed to react under nitrogen at 150° C. for 3 hours and at 230° C. for about 4 hours to yield a clear, liquid mixture. A total of 194 g of the distillate was collected in the Dean-Stark trap. The resulting mixture was allowed to cool to room temperature and subsequently collected (890 g). Glass transition temperature (Tg): −67.6° C.; number average molecular weight (Mn): 1174 g/mole; weight average molecular weight (Mw): 2272 g/mole.

Example 6. Formulation and Evaluation of Curable Compositions

A formulations was prepared by using the liquid like malonate polyester above without solvents and the crosslinker, a mixture of 1,3- and 1,4-cyclohexanedicarboxaldehyde (CHDAL). The catalyst, 1,8-diazabicyclo-[5.4.0]undec-7-ene (DBU) (neat), was used to the formulation to evaluate its effect on curing. The polyester was first mixed with CHDAL at 1:1 equivalent ratio of malonate/CHO functionalities; the catalyst was then added and mixed well. The catalyst was used at a level of 1.5 weight percent based on the total weight of polyester and CHDAL. It was found that the formulation turned viscous after mixing, while no significant color change was observed.

The formulation was allowed to cure at room temperature for 15 hours and its melt viscosity determined by a cone and plate viscomether (CAP 2000 Viscometer by BYK Gardner). It was found that the formulation had the viscosity of 2.6 Pascal-second (measured at 50° C. using spindle cone No. 5 and speed 900 rpm). Separately, the melt viscosity of the malonate polyester was determined to be 0.27 Pascal-second, indicating the occurrence of crosslinking of the formulation over time.

The invention has been described in detail with particular reference to preferred embodiments thereof, but it will be understood that variations and modifications can be effected within the spirit and scope of the invention.

We claim:

1. A curable composition comprising:
   I. a first component having two or more functional groups selected from the group consisting of β-ketoacetate and malonate functional groups;
   II. a second component vinyl polymer having two or more aldehyde functional groups; and
   III. a basic catalyst.

2. The composition of claim 1, wherein the ratio of the ketoacetate and/or malonate-functionalities in the first component and the aldehyde functionality in the second component is from about 1.05 to about 1.0.

3. The composition of claim 1, wherein the first component is a polyester having two or more beta-ketotoacetate groups, or two or more malonate groups or both beta-ketotoacetate groups and malonate groups.

4. The composition of claim 1, wherein the first component is a polyester having two or more beta-ketotoacetate groups.

5. The composition of claim 1, wherein the basic catalyst is one or more selected from the group consisting of 1,8-diazabicyclo-[5.4.0]undec-7-ene (DBU), 1,5-diazabicyclo [4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), 1,1,3,3-tetramethylguanidine (TMG), 1,4-diazabicyclo[2.2.2]octane (DABCO), triethylamine, N,N-dimethylethanolamine, ammonium hydroxide, triphenylphosphine, and tributyl phosphine.

6. The composition of claim 1, wherein the basic catalyst is in an amount ranging from 0.5 to 5 weight % based on the total weight of (I) and (II).

7. The composition of claim 1 further comprising one or more organic solvents selected from the group comprising xylene, methyl amyl ketone, methyl ethyl ketone, 2-butoxyethanol, ethyl-3-ethoxypropionate, toluene, propanol, butanol, cyclopentanone, cyclohexanone, ethyl acetate, and butyl acetate.

8. A curable composition comprising:
   I. a first component adduct having two or more β-ketoacetate functional groups;
   II. a vinyl polymer having two or more aldehyde functional groups; and
   III. a basic catalyst.

9. The composition of claim 8, wherein the adduct is selected from the group comprising 2,2,4,4-tetramethylcyclobutane-1,3-diol diacetoacetate, glycerol triacetoacetate, trimethylpropane triacetoacetate, pentaerythritol tetraacetoacetate.

10. A curable composition comprising:
    I. a first component acetoacetate functional polyester comprising the residues of
       a. a hydroxyl component comprising:
          i. a diol in an amount ranging from 70 to 100 mole %, based on the total moles of (i) and (ii); and
          ii. a polyol in an amount ranging from 0 to 30 mole %, based on the total moles of (i) and (ii);
       b. a carboxyl component comprising a polycarboxylic acid compound, a derivative of polycarboxylic acid compound, or a combination thereof; and
       c. an alkyl acetoacetate, a diketene, or a combination thereof in an amount ranging from about 5 to about 50 weight %, based on the total weight of (a), (b), and (c);
    II. a second component having two or more aldehyde functional groups; and
    III. a basic catalyst;
    wherein the second component is selected from the group comprising 1,3-cyclohexanedicarboxaldehyde (1,3-CHDAL), 1,4-cyclohexanedicarboxaldehyde (1,4-CHDAL), mixtures of 1,3- and 1,4-CHDAL, 2,6-norbornanedicarboxaldehyde, 2,5-norbornane-dicarboxaldehyde, cyclododecane-1,4,8-tricarbaldehyde, 3,(4-formylcyclohexyl)propanal, and their isomers.

11. The composition of claim 10, wherein the second component is selected from 1,3-cyclohexanedicarboxaldehyde (1,3-CHDAL), 1,4-cyclohexane-dicarboxaldehyde (1,4-CHDAL), and mixtures of 1,3- and 1,4-CHDAL.

12. The composition of claim 11, wherein the equivalent ratio of the acetoacetate (AcAc) functionality in the first component and the aldehyde (CHO) functionality in the second component is from about 1.05 to about 1.0.

13. A curable composition comprising:
    I. a polyester comprising the residues of:
       a. a hydroxyl component comprising:
          i. a diol in an amount ranging from 70 to 100 mole %, based on the total moles of (i) and (ii); and ii. a polyol in an amount ranging from 0 to 30 mole %, based on the total moles of (i) and (ii); and b. malonic acid, its ester, or a combination thereof; and c. optionally a carboxyl component, other than malonic acid or its ester, comprising a polycarboxylic acid compound, a derivative of polycarboxylic acid compound, or a combination thereof;

II. an aldehyde component selected from the group consisting of 1,3-cyclohexanedicarboxaldehyde (1,3-CH-DAL), 1,4-cyclohexanedicarboxaldehyde (1,4-CH-DAL), mixtures of 1,3- and 1,4-CHDAL, 2,6-norbornanedicarboxaldehyde, 2,5-norbornanedicarboxaldehyde, cyclododecane-1,4,8-tricarbaldehyde, 3,(4-formylcyclohexyl)propanal, and their isomers; and III. a basic catalyst that is one or more selected from the group consisting of 1,8-diazabicyclo-[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), 1,1,3,3-tetramethylguanidine (TMG), 1,4-diazabicyclo[2.2.2]octane (DABCO), triethylamine, N,N-dimethylethanolamine, ammonium hydroxide, triphenyl phosphine, and tributyl phosphine.

14. A curable composition comprising:

I. an acetoacetate functional polyester comprising the residues of:

a. a hydroxyl component comprising:
   i. a diol in an amount ranging from 70 to 100 mole %, based on the total moles of (i) and (ii); and
   ii. a polyol in an amount ranging from 0 to 30 mole %, based on the total moles of (i) and (ii);

b. a carboxyl component comprising a polycarboxylic acid compound, a derivative of polycarboxylic acid compound, or a combination thereof; and c. an alkyl acetoacetate, a diketene, or a combination thereof in an amount ranging from about 5 to about 50 weight %, based on the total weight of (a), (b), and (c);

II. an aldehyde component selected from the group consisting of 1,3-cyclohexanedicarboxaldehyde (1,3-CH-DAL), 1,4-cyclohexanedicarboxaldehyde (1,4-CH-DAL), mixtures of 1,3- and 1,4-CHDAL, 2,6-norbornanedicarboxaldehyde, 2,5-norbornanedicarboxaldehyde, cyclododecane-1,4,8-tricarbaldehyde, 3,(4-formylcyclohexyl)propanal, and their isomers; and III. a basic catalyst that is one or more selected from the group consisting of 1,8-diazabicyclo-[5.4.0]undec-7-ene (DBU), 1,5-diazabicyclo[4.3.0]non-5-ene (DBN), 1,5,7-triazabicyclo[4.4.0]dec-5-ene (TBD), 7-methyl-1,5,7-triazabicyclo[4.4.0]dec-5-ene (MTBD), 1,1,3,3-tetramethylguanidine (TMG), 1,4-diazabicyclo[2.2.2]octane (DABCO), triethylamine, N,N-dimethylethanolamine, ammonium hydroxide, triphenyl phosphine, and tributyl phosphine.

\* \* \* \* \*